US00PP21994P2

(12) United States Plant Patent

Klemm et al.

(10) Patent No.: US PP21,994 P2

(45) Date of Patent: Jun. 28, 2011

(54) *PETUNIA* PLANT NAMED 'KLEPH09191'

(50) Latin Name: ***Petunia* hybrid**
Varietal Denomination: KLEPH09191

(75) Inventors: Nils Klemm, Stuttgart (DE); Anita Stoever, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/661,845

(22) Filed: Mar. 25, 2010

(51) Int. Cl.
*A01H 5/00* (2006.01)

(52) U.S. Cl. ..... Plt./356

(58) Field of Classification Search ..... Plt./356
See application file for complete search history.

*Primary Examiner* — Kent L Bell

(74) *Attorney, Agent, or Firm* — Jondle & Associates, P.C.

(57) ABSTRACT

A new variety of *Petunia* named 'KLEPH09191' particularly characterized by its double, purple-violet flowers and compact, semi-trailing growth habit, is disclosed.

1 Drawing Sheet

Genus and species: *Petunia* hybrid.
Variety denomination: 'KLEPH09191'.

BACKGROUND OF THE NEW PLANT

The present invention comprises a new and distinct variety of *Petunia*, botanically known as *Petunia* hybrid, and hereinafter referred to by the variety name 'KLEPH09191'. 'KLEPH09191' was discovered as a seedling resulting from a cross conducted in summer 2006 in Stuttgart, Germany between the proprietary female *Petunia* plant, 'PH06 0001' (unpatented) and the proprietary male *Petunia* plant, 'PH06 0048' (unpatented). A single plant selection was subsequently chosen for further evaluation and for asexual propagation.

The new variety was first propagated via vegetative cuttings in summer 2006 in Stuttgart, Germany and has been asexually reproduced repeatedly by vegetative cuttings and in-vitro propagation in Stuttgart, Germany for more than 45 generations. 'KLEPH09191' has been found to retain its distinctive characteristics through successive asexual propagations.

SUMMARY OF THE INVENTION

The following are the most outstanding and distinguishing characteristics of this new variety when grown under normal commercial practices in a greenhouse in Stuttgart, Germany.

1. Double, purple-violet flowers; and
2. Compact, semi-trailing growth habit.

DESCRIPTION OF THE PHOTOGRAPH

This new *Petunia* plant is illustrated by the accompanying photograph which shows a close-up of a mature flower. The colors shown are as true as can be reasonably obtained by conventional photographic procedures. The photograph was taken in May 2009 of a 5-month-old plant grown from rooted cuttings in an 11 centimeter pot in a greenhouse (glasshouse) in Stuttgart, Germany under conditions which approximate those generally used in commercial practice.

DESCRIPTION OF THE NEW VARIETY

The following detailed descriptions set forth the distinctive characteristics of 'KLEPH09191'. The data which define these characteristics were collected from asexual reproductions carried out in Stuttgart, Germany. The plant history was taken in May 2009 on 5-month-old plants in 11 centimeter pots that were pinched once approximately one week after potting and grown in a greenhouse. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Solanaceae.
- *Genus and species.*—*Petunia* hybrid.
- *Common name.*—*Petunia.*

Parentage:
- *Female parent.*—The proprietary *Petunia* 'PH06 0001' (unpatented).
- *Male parent.*—The proprietary *Petunia* 'PH06 0048' (unpatented).

Plant:
- *Form.*—Compact.
- *Habit.*—Semi-trailing.
- *Height (from top of soil).*—13.0 cm.
- *Width (horizontal plant diameter).*—16.0 cm.
- *Propagation.*—Vegetative propagation by terminal tip cuttings or in-vitro propagation of shoot tips.
- *Time to produce a finished flowering plant.*—11 weeks.
- *Time to initiate and develop roots.*—16 days.
- *Root description.*—Moderate density and moderate branching, white roots.

Stems:
- *Average number (basal).*—5.
- *Length of basal branches (from the base of the stem to the tip).*—8.0 cm.
- *Internode length.*—1.5 cm to 2.5 cm.
- *Diameter of branches (from midpoint).*—4.0 mm to 10.0 mm.
- *Stem color.*—RHS 144B.
- *Anthocyanin.*—Absent.
- *Texture.*—Smooth.

Leaves:

*Arrangement.*—Alternate.

*Size.*—Length: 3.0 cm to 5.0 cm. Width: 1.5 cm to 3.0 cm.

*Shape.*—Broadly elliptic.

*Margin.*—Weak undulation.

*Apex.*—Acute.

*Base.*—Obtuse.

*Immature and mature leaf.*—Color: Upper surface: RHS 143A. Lower surface: RHS 138B.

*Texture* (*both upper and lower surfaces*).—Smooth.

*Venation pattern.*—Pinnate. Venation color: Upper surface: RHS 144B. Lower surface: RHS 144C.

*Petioles.*—Length: 0.2 cm to 1.0 cm. Diameter: 0.2 cm. Color: Upper surface: RHS 143A. Lower surface: RHS 138B. Texture: Smooth.

Flower bud:

*Shape.*—Irregular to oblong.

*Size.*—Length: 3.5 cm. Diameter: 2.5 cm.

*Color at tight bud.*—RHS N186D.

*Immature flower color.*—RHS N186C.

*Texture* (*both upper and lower surfaces*).—Smooth.

Inflorescence:

*Blooming habit* (*flowering season*).—Continuous flowering during the summer.

*Inflorescence type.*—Double flowering.

*Number of flowers per node.*—1.

*Lastingness of individual blooms on the plant.*—7 days.

*Fragrance.*—Absent.

*Pedicels.*—Color: RHS 144A. Length: 2.0 cm. Diameter: 0.3 cm. Texture: Smooth.

Flowers:

*Shape.*—Cup-shaped.

*Size.*—Diameter (flower face): 5.5 cm. Depth (total length of flower): 5.0 cm. Funnel: Length: 2.5 cm. Diameter (at opening): 1.5 cm. Outside texture: Smooth.

*Mature flower.*—Face/Margin color: Upper surface: RHS N81A. Lower surface: RHS N81C. Corolla tube: Shape: Funnel-shaped. Color inside (throat): RHS N77A. Color outside: RHS N77B. Petals: Number: 18. Apex: Rounded to emarginate. Base: Uniform. Margin: Entire, slightly undulating. Waviness: Medium. Lobation: Medium. Texture (both upper and lower surfaces): Smooth.

*Calyx arrangement.*—Actinomorphic.

*Sepals.*—Number: 5. Color: Upper surface: RHS 138A. Lower surface: RHS 138B. Length: 1.5 cm. Width: 0.4 cm. Shape: Lanceolate. Apex: Obtuse. Base: Open. Margin: Entire Texture (both upper and lower surfaces): Smooth.

Reproductive organs:

*Stamens.*—Quantity: 5. Shape: Needlelike with elliptic head. Filament: Length: 1.2 cm. Diameter: 0.1 cm. Color: RHS 189D.

*Anther.*—Shape: Elliptic. Color: RHS 189D. Length: 0.2 cm. Diameter: 0.2 cm.

*Pollen.*—Color: RHS 188D. Amount: Sparse.

*Pistils.*—Absent.

Fruit and seed set: None observed.

Disease and insect resistance: No common diseases observed.

COMPARISON WITH PARENTAL AND COMMERCIAL VARIETIES

'KLEPH09191' differs from the female parent, the proprietary *Petunia* 'PH06 0001' (unpatented), in that 'KLEPH09191' has double, purple-colored flowers, while 'PH06 0001' has single, blue-colored flowers.

'KLEPH09191' differs from the male parent, the proprietary *Petunia* 'PH06 0048' (unpatented), in that 'KLEPH09191' has double, purple-colored flowers, while 'PH06 0048' has double, red-colored flowers.

'KLEPH09191' differs from the commercial comparison variety, the proprietary *Petunia* 'PH06 0128' (unpatented), in that 'KLEPH09191' has purple-violet colored flowers (RHS N81A), while 'PH06 0128' has dark, blue-colored flowers (RHS 89B).

We claim:

1. A new and distinct variety of *Petunia* plant named 'KLEPH09191' as shown and described herein.

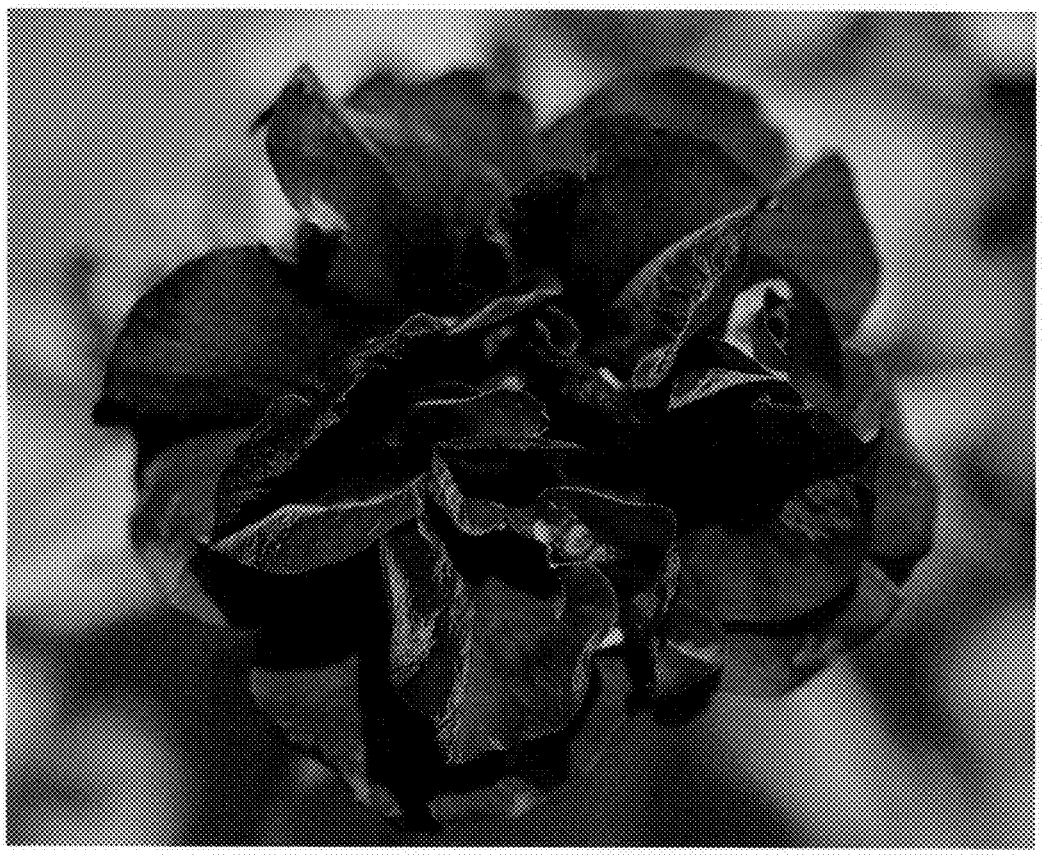

* * * * *